United States Patent
Yang

(10) Patent No.: US 10,426,793 B2
(45) Date of Patent: Oct. 1, 2019

(54) MEDICATION AND APPLICATION FOR TREATMENT OF HYPERTENSION BASED ON ANION AND TRADITIONAL CHINESE MEDICINE

(71) Applicant: Peng Yang, Huizhou (CN)

(72) Inventor: Peng Yang, Huizhou (CN)

(*) Notice: Subject to any disclaimer, the term of this patent is extended or adjusted under 35 U.S.C. 154(b) by 463 days.

(21) Appl. No.: 15/204,704

(22) Filed: Jul. 7, 2016

(65) Prior Publication Data

US 2017/0007641 A1  Jan. 12, 2017

(30) Foreign Application Priority Data

Jul. 7, 2015 (CN) .......................... 2015 1 0392999

(51) Int. Cl.

| | | |
|---|---|---|
| *A61K 33/00* | (2006.01) | |
| *A61K 36/539* | (2006.01) | |
| *A61K 36/233* | (2006.01) | |
| *A61K 36/74* | (2006.01) | |
| *A61K 36/258* | (2006.01) | |
| *A61K 36/24* | (2006.01) | |
| *A61K 36/068* | (2006.01) | |
| *A61K 36/481* | (2006.01) | |
| *A61K 36/062* | (2006.01) | |
| *A61K 36/486* | (2006.01) | |
| *A61K 36/48* | (2006.01) | |
| *A61K 9/06* | (2006.01) | |
| *A61K 9/20* | (2006.01) | |
| *A61K 9/14* | (2006.01) | |

(52) U.S. Cl.
CPC ................ *A61K 33/00* (2013.01); *A61K 9/06* (2013.01); *A61K 9/14* (2013.01); *A61K 9/20* (2013.01); *A61K 36/062* (2013.01); *A61K 36/068* (2013.01); *A61K 36/233* (2013.01); *A61K 36/24* (2013.01); *A61K 36/258* (2013.01); *A61K 36/48* (2013.01); *A61K 36/481* (2013.01); *A61K 36/486* (2013.01); *A61K 36/539* (2013.01); *A61K 36/74* (2013.01)

(58) Field of Classification Search
None
See application file for complete search history.

(56) References Cited

PUBLICATIONS

Remington's. "Remington's Pharmaceutical Science 17th Edition". Gannaro, A (Ed.). pp. 1480, 1492, 1516, 1517,1585. (Year: 1985).*

* cited by examiner

*Primary Examiner* — Amy L Clark
(74) *Attorney, Agent, or Firm* — Novoclaims Patent Services LLC; Mei Lin Wong

(57) ABSTRACT

A medicament for treatment of hypertension based on anion and traditional Chinese medicine, containing active ingredients by percentage weight, which are: 9~30% of *Scutellaria baicalensis*, 3~9% of *Radix bupleuri*, 3~12% of *Uncaria tomentosa* (cat's claw), 3~9% of Ginseng, 15~25% of *Cynanchum mooreanum* Hemsl., 3~9% of *Cordyceps sinensis* (Berk.) Sacc., 10~15% of *Flastem Milkvetch* Seed, 9~15% of *Dermatocarpon miniatum* (L.) Mann. [*Lichen miniatius* L.], 10~15% of *Millettia dielsiana*, 10~15% of stem or root of *Dalbergia hancei* Benth. (Leguminosae), 1~4% of anion powder and 1~4% of far-infrared nano powder. Through the use of far infrared nano powder and anion powder with low cost and easily obtainable traditional Chinese medicine, the traditional Chinese medicine is further strengthened with increased efficacy while the far infrared and anion promotes blood circulation and cell repair, which in turn further increases the efficacy and treatment result.

2 Claims, No Drawings

MEDICATION AND APPLICATION FOR TREATMENT OF HYPERTENSION BASED ON ANION AND TRADITIONAL CHINESE MEDICINE

CROSS REFERENCE OF RELATED APPLICATION

This is a non-provisional application which claimed priority of Chinese application number 201510392999.3, filing date Jul. 7, 2015. The contents of this specification, is incorporated herein by reference.

BACKGROUND OF THE PRESENT INVENTION

Field of Invention

The present invention relates a medicament for treatment of hypertension.

Description of Related Arts

Anion medicine is a basic science which includes a collection of different subjects such as electronics, chemistry, materials science, polymer science, life science and clinical science. Anion is also referred to as negative oxygen ion, which is an oxygen ion carrying one or more negatively charged electron. The vast majority of negative ions generated in the air is atmospheric negative oxygen ions, which is formed from combining the oxygen molecules in the air with free electron. The electric discharge (lightning) phenomenon in nature, the photoelectric effect the fountains, waterfalls and etc. can induce ionization in the ambient air to form the negative oxygen ions. Anion (negative ions) has excellent purification and dust removal effect and can reduce the hazards of passive smoking, improve and prevent respiratory disease, improve sleeping quality, provide anti-oxidation and anti-aging effect, eliminate free radicals in the body and reduce blood viscosity. In the medical profession, it has a reputation of naming as 'vita oxygen', 'air vitamins', 'longevity element' and 'ambient vitamins'.

The healthcare principle of anion is mainly due to the prominent role of the anion in providing antiaging and antioxidant (reducing) effect. The antioxidant (reducing) effect of anion is under a basic chemical principle. The negative ion is negatively charged. In other words, an excess electron is existed, that this electron can be supply to aging cells and blood cell. Thus, the antiaging and antioxidant effect as well as the radical reduction effect can be achieved. In a living body, if the electrons of lipid is snatched, lipid will be oxidized and age spots are formed. If the electrons of protein is snatched, the cell function will become abnormal. If the electrons of a gene is snatched, the disease of cancer will be induced. In the living body, the substance which snatches electrons are called 'free radicals'. From the view of quantum medicine, the snatching of electrons is the origin of all diseases. Similarly, the rusting of iron, the weathering of rocks and the rotting of plant are all the result of oxidation. The negative oxygen ions are charged with negative potential, that is, an excess electron. The electron is supplied to the free radicals and then the free radicals are reduced. In other word, the free radicals are eliminated. Then, the negative oxygen ions itself are transformed into oxygen molecules $O_2$.

Hypertension is now a common disease easily occurred in many people and its symptoms vary according to the object conditions. In the early stage, it may be asymptomatic or the symptom is not obvious. The object may feel fatigue and nervous, or the blood pressure increases after mood swings and then return to normal after taking a rest. As the course of disease is extended, the blood pressure is persistently elevated significantly and a variety of symptoms will be occurred gradually. At this stage, it is called chronic hypertension. The common clinical symptoms of chronic hypertension disease includes headache, dizziness, concentration difficulties, memory loss, numbness, nocturia, palpitation, chest tightness and fatigue. When the blood pressure is suddenly increased to a certain high level, symptoms such as severe headache, vomiting, palpitation and dizziness may even occur. In severe cases, unconsciousness and convulsions will be happened. At this stage, it is called accelerated hypertension and hypertensive crisis. In general, serious heart, brain and kidney damages and diseases such as stroke, myocardial infarction and renal failure will follow in a short period of time. There is no consistent relationship between the symptoms and the blood pressure level. In view of the treatment of hypertension, in additional to physical conditioning such as weight loss, antihypertensive drugs can be used. However, this kind of drug must be taken every day and has strong dependence.

SUMMARY OF THE PRESENT INVENTION

In order to solve the problems of existing arts, an object of the present invention is to provide a medicament for treatment of hypertension based on anion and Traditional Chinese medicine which is effective and quick without any side effects.

Additional advantages and features of the invention will become apparent from the description which follows, and may be realized by means of the instrumentalities and combinations particular point out in the appended claims.

According to the present invention, the foregoing and other objects and advantages are attained by the followings:

A medicament for treatment of hypertension based on anion and traditional Chinese medicine, containing active ingredients by percentage weight, which are: 9~30% of *Scutellaria baicalensis*, 3~9% of *Radix bupleuri*, 3~12% of *Uncaria tomentosa* (cat's claw), 3~9% of Ginseng, 15~25% of *Cynanchum mooreanum* Hemsl., 3~9% of *Cordyceps sinensis* (Berk.) Sacc., 10~15% of *Flastem Milkvetch* Seed, 9~15% of *Dermatocarpon miniatum* (L.) Mann. [*Lichen miniatius* L.], 10~15% of *Millettia dielsiana*, 10~15% of stem or root of *Dalbergia hancei* Benth. (Leguminosae), 1~4% of anion powder and 1~4% of far-infrared nano powder.

Preferably, the medicament in one single unit contains 9~30 g of *Scutellaria baicalensis*, 3~9 g of *Radix bupleuri*, 3~12 g of *Uncaria tomentosa* (cat's claw), 3~9 g of Ginseng, 15~25 g of *Cynanchum mooreanum* Hemsl., 3~9 g of *Cordyceps sinensis* (Berk.) Sacc., 10~15 g of *Flastem Milkvetch* Seed, 9~15 g of *Dermatocarpon miniatum* (L.) Mann. [*Lichen miniatius* L.], 10~15 g of *Millettia dielsiana*, 10~15 g of stem or root of *Dalbergia hancei* Benth. (Leguminosae), 1~4 g of anion powder and 1~4 g of far-infrared nano powder.

In addition, the application of the medicament for treatment of hypertension based on anion and traditional Chinese medicine are provided as follows:

An ointment for treatment of hypertension based on anion and traditional Chinese medicine, containing active ingredients by percentage weight, which are: 9~30% of *Scutellaria baicalensis*, 3~9% of *Radix bupleuri*, 3~12% of *Uncaria tomentosa* (cat's claw), 3~9% of Ginseng, 15~25% of *Cynanchum mooreanum* Hemsl., 3~9% of *Cordyceps sinensis* (Berk.) Sacc., 10~15% of *Flastem Milkvetch* Seed, 9~15% of *Dermatocarpon miniatum* (L.) Mann. [*Lichen miniatius* L.], 10~15% of *Millettia dielsiana*, 10~15% of stem or root of *Dalbergia hancei* Benth. (Leguminosae), 1~4% of anion powder and 1~4% of far-infrared nano powder, wherein the ointment is prepared by mixing said active ingredients and a ointment base to form the ointment.

Preferably, the medicament in one single unit contains 9~30 g of *Scutellaria baicalensis*, 3~9 g of *Radix bupleuri*, 3~12 g of *Uncaria tomentosa* (cat's claw), 3~9 g of Ginseng, 15~25 g of *Cynanchum mooreanum* Hemsl., 3~9 g of *Cordyceps sinensis* (Berk.) Sacc., 10~15 g of *Flastem Milkvetch* Seed, 9~15 g of *Dermatocarpon miniatum* (L.) Mann. [*Lichen miniatius* L.], 10~15 g of *Millettia dielsiana*, 10~15 g of stem or root of *Dalbergia hancei* Benth. (Leguminosae), 1~4 g of anion powder and 1~4 g of far-infrared nano powder.

According to another application of the medicament, the present invention provides an ointment for treatment of hypertension based on anion and traditional Chinese medicine, wherein the ointment comprises a first layer and a second layer, wherein the first layer is a layer of traditional Chinese medicine which is arranged for direct contact with skin of an object and the second layer is a radiation layer of far-infrared and anion exterior to the first layer, wherein the first layer contains active ingredients by percentage weight, which are: 9~30% of *Scutellaria baicalensis*, 3~9% of *Radix bupleuri*, 3~12% of *Uncaria tomentosa* (cat's claw), 3~9% of Ginseng, 15~25% of *Cynanchum mooreanum* Hemsl., 3~9% of *Cordyceps sinensis* (Berk.) Sacc., 10~15% of *Flastem Milkvetch* Seed, 9~15% of *Dermatocarpon miniatum* (L.) Mann. [*Lichen miniatius* L.], 10~15% of *Millettia dielsiana* and 10~15% of stem or root of *Dalbergia hancei* Benth. (Leguminosae), wherein the second layer contains active ingredients by percentage weight, which are: 1~4% of anion powder and 1~4% of far-infrared nano powder.

Preferably, the ointment in one single unit contains active ingredients of 9~30 g of *Scutellaria baicalensis*, 3~9 g of *Radix bupleuri*, 3~12 g of *Uncaria tomentosa* (cat's claw), 3~9 g of Ginseng, 15~25 g of *Cynanchum mooreanum* Hemsl., 3~9 g of *Cordyceps sinensis* (Berk.) Sacc., 10~15 g of *Flastem Milkvetch* Seed, 9~15 g of *Dermatocarpon miniatum* (L.) Mann. [*Lichen miniatius* L.], 10~15 g of *Millettia dielsiana* and 10~15 g of stem or root of *Dalbergia hancei* Benth. (Leguminosae) for the first layer and 1~4 g of anion powder and 1~4 g of far-infrared nano powder for the second layer.

Preferably, the active ingredients of the first layer and the second layer are brewed separately with ointment base and are adhered to two soft carriers respectively such that an inner layer and an outer layer which can be used independently are formed.

Preferably, wherein the active ingredients of the first layer and the second layer are brewed separately with ointment base respectively. Then the first layer is bonded to the second layer such that the first layer and the second layer are combined to form an integrated structure and are adhered to a soft carrier through the second layer.

Preferably, the active ingredients of the first layer are brewed with ointment base and then adhered to a soft carrier, wherein the active ingredients of the second layer are mixed and grounded into powder and is adhered to an external side of the first layer.

According to another application of the preferred embodiment of the present invention, the present invention provides a pill form medicament for treatment of hypertension based on anion and traditional Chinese medicine, containing active ingredients by percentage weight, which are: 9~30% of *Scutellaria baicalensis*, 3~9% of *Radix bupleuri*, 3~12% of *Uncaria tomentosa* (cat's claw), 3~9% of Ginseng, 15~25% of *Cynanchum mooreanum* Hemsl., 3~9% of *Cordyceps sinensis* (Berk.) Sacc., 10~15% of *Flastem Milkvetch* Seed, 9~15% of *Dermatocarpon miniatum* (L.) Mann. [*Lichen miniatius* L.], 10~15% of *Millettia dielsiana*, 10~15% of stem or root of *Dalbergia hancei* Benth. (Leguminosae), 0.1~1% of anion powder and 0.1~1% of far-infrared nano powder, wherein a particle size requirement of the anion powder and the far-infrared nano powder is 2000~4000 mesh. Preferably, the pill form is prepared by combining the active ingredients and excipient through a conventional pill production process of Traditional Chinese medicine to obtain the pill form medicament.

Preferably, pill form medicament contains active ingredients of: 9~30 g of *Scutellaria baicalensis*, 3~9 g of *Radix bupleuri*, 3~12 g of *Uncaria tomentosa* (cat's claw), 3~9 g of Ginseng, 15~25 g of *Cynanchum mooreanum* Hemsl., 3~9 g of *Cordyceps sinensis* (Berk.) Sacc., 10~15 g of *Flastem Milkvetch* Seed, 9~15 g of *Dermatocarpon miniatum* (L.) Mann. [*Lichen miniatius* L.], 10~15 g of *Millettia dielsiana*, 10~15 g of stem or root of *Dalbergia hancei* Benth. (Leguminosae), 0.1~1 g of anion powder and 0.1~1 g of far-infrared nano powder.

According to another application of the preferred embodiment of the present invention, the present invention provides a powder form medicament containing active ingredients by percentage weight, which are: 9~30% of *Scutellaria baicalensis*, 3~9% of *Radix bupleuri*, 3~12% of *Uncaria tomentosa* (cat's claw), 3~9% of Ginseng, 15~25% of *Cynanchum mooreanum* Hemsl., 3~9% of *Cordyceps sinensis* (Berk.) Sacc., 10~15% of *Flastem Milkvetch* Seed, 9~15% of *Dermatocarpon miniatum* (L.) Mann. [*Lichen miniatius* L.], 10~15% of *Millettia dielsiana*, 10~15% of stem or root of *Dalbergia hancei* Benth. (Leguminosae), 1~4% of anion powder and 1~4% of far-infrared nano powder. The powder form is prepared by grinding the active ingredients into powder having a size of 200~1000 mesh. Preferably, the active ingredients in powder form is loaded into a bag to obtain a bagged powder form of the medicament.

Preferably, one single unit of the powder form medicament contains active ingredients of: 9~30 g of *Scutellaria baicalensis*, 3~9 g of *Radix bupleuri*, 3~12 g of *Uncaria tomentosa* (cat's claw), 3~9 g of Ginseng, 15~25 g of *Cynanchum mooreanum* Hemsl., 3~9 g of *Cordyceps sinensis* (Berk.) Sacc., 10~15 g of *Flastem Milkvetch* Seed, 9~15 g of *Dermatocarpon miniatum* (L.) Mann. [*Lichen miniatius* L.], 10~15 g of *Millettia dielsiana*, 10~15 g of stem or root of *Dalbergia hancei* Benth. (Leguminosae), 1~4 g of anion powder and 1~4 g of far-infrared nano powder.

According to the present invention, anion powder, far-infrared powder and other active ingredients which are easily accessible and relatively low cost are used. Through the use of anion and far-infrared, the medicinal properties of the Chinese medicine are further strengthened such that the effectiveness is enhanced. Meanwhile, anion and far-infrared can effectively promote blood circulation and cell repair. Thus, the efficacy of the pharmacodynamics of the active ingredients are further promoted and the treatment effect of hypertension is further enhanced.

According to the present invention, the present invention can be brewed directly into a decoction for drinking or prepared into different forms such as ointment, pill or bagged powder. When using the medicament of the present invention, the different forms can be used alone or in combination as needed to further ensure the provision of treatment effect.

For the ointment form, far infrared and anion are released by the radiation layer and penetrate through the layer of traditional Chinese medicine to penetrate through the surface tissue layer of human object. At the same time, the active ingredients of the traditional Chinese medicine are entered into the human object through the surface tissue layer of human object to reach the focus of the affected area directly. Accordingly, a quick result and an enhanced penetration of the traditional Chinese medicine is achieved, thus the efficacy is increased. When the ointment is prepared into two independent layer structure, the outer layer can be re-used repeatedly while the inner layer can be replaced based on the efficacy period of the traditional Chinese medicine, which is convenience to use.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The medicament for treatment of hypertension based on anion and traditional Chinese medicine and its application method according to the preferred embodiment of the present invention is further described as follows.

According to the preferred embodiment of the present invention, the medicament for treatment of hypertension based on anion and traditional Chinese medicine is formulated according to the following composition and weight: 19 g *Scutellaria baicalensis*, 6 g *Radix bupleuri*, 8 g *Uncaria tomentosa* (cat's claw), 6 g Ginseng, 20 g *Cynanchum mooreanum* Hemsl., 6 g *Cordyceps sinensis* (Berk.) Sacc., 13 g *Flastem Milkvetch* Seed, 12 g *Dermatocarpon miniatum* (L.) Mann. [*Lichen miniatius* L.], 13 g *Millettia dielsiana,* 13 g stem or root of *Dalbergia hancei* Benth. (Leguminosae), 3 g anion powder and 3 g far-infrared nano powder.

According to this preferred embodiment of the present invention, *Scutellaria baicalensis* can provide anti-inflammatory, anti-allergic, liver and gall bladder protection, lower blood pressure, diuretic, sedative and antipyretic effect. *Radix bupleuri* has the effect of reconciling superficies and interior, relaxation of liver and dispel depression, raise 'yang' and lift dropping, and antipyretic and preventing malaria. *Uncaria tomentosa* (cat's claw) has the effect of calming, lower blood pressure, heat removal and liver calming, and stop endogenous wind and calm fear. *Sparganium stoloni* serum, Buch-Ham has the effect of expelling blood and promoting 'Qi', dispersing accumulation and relieving pain. The anion powder releases anion which has the effect of antioxidant (reducing) and anti-aging. Clinically, it can prevent diseases such as acute and chronic bronchitis, asthma, hypertension, high cholesterol, coronary heart disease and neurasthenia. The far infrared released from the far infrared nano powder has the effect of activating the activity of biological macromolecules such that molecules of the organism are under the condition of higher vibrational state, blood circulation is promoted and improved, metabolism is increased and immune function is improved. Ginseng has the effect of adjustment blood pressure, restoring cardiac function, treating physical weakness and neurasthenia and etc. It also has expectorant, stomachic, diuretic and excitatory effect. *Cynanchum mooreanum* Hemsl. has the effect of clearing the heat and cooling the blood, promoting the function of gallbladder, detoxification, mastering 'Yin' fever, treating consumptive disease, long-term coughing, hemoptysis, hypochondrium distending pain, nausea and vomiting, diarrhea, postpartum weakness, scrofula, innominate toxin swelling, and bites from snakes, bugs and rabid dogs. *Cordyceps sinensis* (Berk.) Sacc. can enhance immune system of the body, nourish and replenish lung and kidney, and inhibit lung and liver cancer significantly. Clinically, it has the effect of treating lung deficiency and persistent coughing, asthma, tuberculosis hemoptysis, night sweating, kidney weakness, waist and knee pain, impotence and emission, neurasthenia and decreased level of red blood cell after chemotherapy and radiotherapy. *Flastem Milkvetch* Seed has the effect of replenishing liver, nourishing kidney, promoting eyesight and fixing sperms. It can used to treat liver and kidney deficiency, waist and knee pain, head faint, premature emission, frequent urination, enuresis, hematuria and vaginal discharge. *Dermatocarpon miniatum* (L.) Mann. [*Lichen miniatius* L.] has the effect of lowering blood pressure. *Millettia dielsiana* can treat blood coagulation and fibrinolysis of hematopoietic system and heart inhibition, lower blood pressure, provide anticancer effect and regulate lipid metabolism. Stem or root of *Dalbergia hancei* Benth. (Leguminosae) has the effect of treating heart and stomach pain, chronic injury and accumulated pain, and non-traumatic external bleeding and subcutaneous hemorrhage.

According to this preferred embodiment of the present invention, the above composition of the traditional Chinese medicine co-operates with the anion and the far infrared. Through the action of the far infrared on the human object, the traditional Chinese medicine can reach the affected area directly and provide health treatment at multi-angle. At the same time, the efficacy of the traditional Chinese medicine can be strengthened. Accordingly, a quick and effective treatment for hypertension without any side effect can be provided.

According to this preferred embodiment of the present invention, the above composition of the traditional Chinese medicine can be prepared directly through the convention brewing method of the traditional Chinese medicine into a decoction for drinking. The above composition of the traditional Chinese medicine can also be prepared into a plurality of forms such as ointment, pill, powder or bagged powder.

I. Ointment Form

If the medicament is prepared into an ointment, the medicament is formulated according to the following composition and weight: 19 g *Scutellaria baicalensis,* 6 g *Radix Bupleuri,* 8 g *Uncaria tomentosa* (cat's claw), 6 g Ginseng, 20 g *Cynanchum mooreanum* Hemsl., 6 g *Cordyceps sinensis* (Berk.) Sacc., 13 g *Flastem Milkvetch* Seed, 12 g *Dermatocarpon miniatum* (L.) Mann. [*Lichen miniatius* L.], 13 g *Millettia dielsiana,* 13 g stem or root of *Dalbergia hancei* Benth. (Leguminosae), 3 g anion powder and 3 g far-infrared nano powder. The above composition is mixed with an ointment base to form the ointment. (Conventional technology for the ointment base and the preparation method of the ointment base can be used. The ointment base can be a common ointment base such as black ointment base, oil-wax type ointment base and white ointment base, etc. Conventional ointment preparation method can be used to prepare the ointment and is not repeated here)

Preferably, the ointment has a two-layer structure having a first layer and a second layer. The first layer is a layer of traditional Chinese medicine which is arranged for direct contact with skin of human object and the second layer is a radiation layer of far-infrared and anion which is provided at an exterior to the first layer. The first layer, which is the layer of traditional Chinese medicine, contains the following active ingredients: 19 g *Scutellaria baicalensis*, 6 g *Radix bupleuri*, 8 g *Uncaria tomentosa* (cat's claw), 6 g Ginseng, 20 g *Cynanchum mooreanum* Hemsl., 6 g *Cordyceps sinensis* (Berk.) Sacc., 13 g *Flastem Milkvetch* Seed, 12 g *Dermatocarpon miniatum* (L.) Mann. [*Lichen miniatius* L.], 13 g *Millettia dielsiana* and 13 g stem or root of *Dalbergia hancei* Benth. (Leguminosae). The second layer, which is the radiation layer, contains the following active ingredients: 3 g anion powder and 3 g far-infrared nano powder.

Preferably, the two-layer structure of the ointment provides three application methods as follows:

(a) The active ingredients of the first layer and the second layer are brewed separately with ointment base and are adhered to two soft carriers respectively such that an inner layer and an outer layer which can be used independently are formed. In other words, the two layers are physically separated and can be used independently. When use, the first layer, which is the layer of traditional Chinese medicine, can be replaced as needed while the second layer, which is the radiation layer, can be used repeatedly as needed.

(b) The active ingredients of the first layer and the second layer are brewed separately with ointment base respectively. Then the first layer, which is the layer of traditional Chinese medicine, is bonded to the second layer, which is the radiation layer, such that the first layer and the second layer are combined together form an integrated structure and the first layer is adhered to a soft carrier through the second layer.

(c) The active ingredients of the first layer are brewed with ointment base and then adhered to a soft carrier, then the active ingredients of the second layer, which are the anion and the far infrared substance, are mixed and grinded into powder and is adhered to an external side of the first layer.

Preferably, a size of the first layer is the same as or is slightly small than a size of the radiation layer. The first layer can be arranged to stick onto the skin directly or through the second layer covering the first layer to securely adhere onto the skin. In other words, the second layer is covering the first layer and sticking onto the skin such that the first layer is securely positioned onto the skin.

For the ointment form, far infrared and anion are released by the radiation layer and penetrate through the layer of traditional Chinese medicine to penetrate through the surface tissue layer of human object. At the same time, the active ingredients of the traditional Chinese medicine are entered into the human object through the surface tissue layer of human object to reach the focus of the affected area directly. Accordingly, a quick result and an enhanced penetration of the traditional Chinese medicine is achieved, thus the efficacy is increased.

II. Pill Form

If the medicament is prepared into a pill form, the medicament is formulated according to the following composition and weight: 19 g *Scutellaria baicalensis*, 6 g *Radix Bupleuri*, 8 g *Uncaria tomentosa* (cat's claw), 6 g Ginseng, 20 g *Cynanchum mooreanum* Hemsl., 6 g *Cordyceps sinensis* (Berk.) Sacc., 13 g *Flastem Milkvetch* Seed, 12 g *Dermatocarpon miniatum* (L.) Mann. [*Lichen miniatius* L.], 13 g *Millettia dielsiana*, 13 g stem or root of *Dalbergia hancei* Benth. (Leguminosae), 0.5 g anion powder and 0.5 g far-infrared nano powder. The particle size requirement of the anion powder and the far-infrared nano powder is 3000 mesh. The pill form is prepared by combining the active ingredients with excipient (The excipient can use the common excipients for conventional pill form preparation of traditional Chinese medicine, such as water, alcohol, vinegar, honey water, concoction, honey, rice paste and batter paste.) according to the method of preparation of traditional Chinese medicine in pill form (such as the conventional method disclosed by the patent number 201210246297.0) to prepare the medicament in pill form. In the above active ingredients, the content of the anion and the far infrared nano powder is between 0.1 and 1. For examples, the content can be 0.1 g, 0.5 g or 1 g. The mesh size can be 2000 mesh or 4000 mesh. The effectiveness within these ranges has the same technological effect.

III. Powder Form (Packed in a Bag)

If the medicament is prepared into a powder form (and/or packed in a bag), the medicament is formulated according to the following composition and weight: 19 g *Scutellaria baicalensis*, 6 g *Radix bupleuri*, 8 g *Uncaria tomentosa* (cat's claw), 6 g Ginseng, 20 g *Cynanchum mooreanum* Hemsl., 6 g *Cordyceps sinensis* (Berk.) Sacc., 13 g *Flastem Milkvetch* Seed, 12 g *Dermatocarpon miniatum* (L.) Mann. [*Lichen miniatius* L.], 13 g *Millettia dielsiana*, 13 g stem or root of *Dalbergia hancei* Benth. (Leguminosae), 3 g anion powder and 3 g far-infrared nano powder. The active ingredients are grinded into powder having a size of 200~1000 mesh and is loaded into a bag to obtain the medicament in a bagged powder form.

According to another preferred embodiment of the present invention, instead of the above exemplary composition and weight of formulation, the medicament can also has the composition and weight formulation as follows:

9~30 g of *Scutellaria baicalensis*, 3~9 g of *Radix bupleuri*, 3~12 g of *Uncaria tomentosa* (cat's claw), 3~9 g of Ginseng, 15~25 g of *Cynanchum mooreanum* Hemsl., 3~9 g of *Cordyceps sinensis* (Berk.) Sacc., 10~15 g of *Flastem Milkvetch* Seed, 9~15 g of *Dermatocarpon miniatum* (L.) Mann. [*Lichen miniatius* L.], 10~15 g of *Millettia dielsiana*, 10~15 g of stem or root of *Dalbergia hancei* Benth. (Leguminosae), 1~4 g of anion powder and 1~4 g of far-infrared nano powder. All the ranges are indicated inclusively. For examples, the range of 9~30 g includes 9 and 30, the range of 3~9 g includes 3 and 9, and etc. All the above composition and weight can achieve the technological results of the present invention.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A medicament for treatment of hypertension comprising: 9~30% by percentage weight of *Scutellaria baicalensis*, 3~9% by percentage weight of *Radix Bupleuri*, 3~12% by percentage weight of *Uncaria tomentosa* (cat's claw), 3~9% by percentage weight of Ginseng, 15~25% by percentage weight of *Cynanchum mooreanum* Hemsl., 3~9% by percentage weight of *Cordyceps sinensis* (Berk.) Sacc., 10~15% by percentage weight of *Flastem Milkvetch* Seed, 9~15% by percentage weight of *Dermatocarpon miniatum*

(L.) Mann. [*Lichen miniatius* L.], 10~15% by percentage weight of *Millettia dielsiana,* 10~15% by percentage weight of stem or root of *Dalbergia hancei* Benth. (Leguminosae), 0.1~1% by percentage weight of anion powder and 0.1~1% by percentage weight of far-infrared nano powder, wherein the particle size of said anion powder and said far-infrared nano powder is 2000~4000 mesh, and wherein said medicament for treatment of hypertension is in the form of a pill.

2. The medicament for treatment of hypertension according to claim 1, further comprising an excipient.

* * * * *